United States Patent [19]

Arena

[11] Patent Number: 4,900,667
[45] Date of Patent: Feb. 13, 1990

[54] ONE CARBON HOMOLOGATION OF CARBOHYDRATES BY TRANSCYANOHYDRINATION

[75] Inventor: Blaise J. Arena, Des Plaines, Ill.

[73] Assignee: Allied-Signal Inc., Morris Township, Morris County, N.J.

[21] Appl. No.: 73,259

[22] Filed: Jul. 13, 1987

Related U.S. Application Data

[63] Continuation-in-part of Ser. No. 810,627, Dec. 19, 1985, abandoned.

[51] Int. Cl.$^4$ .............................................. C12P 19/26
[52] U.S. Cl. ...................................... 435/84; 435/128; 536/55.3; 558/351; 558/451; 558/410
[58] Field of Search ...................... 435/84, 85, 128, 41, 435/232; 558/351, 410, 451; 536/55.3

[56] References Cited

U.S. PATENT DOCUMENTS

| | | | |
|---|---|---|---|
| 2,259,167 | 10/1941 | Kung | 260/464 |
| 4,048,210 | 9/1977 | Davis | 260/465 F |
| 4,246,189 | 1/1981 | Kleemann et al. | 558/451 X |

OTHER PUBLICATIONS

W. Becker, H. Freund, and E. Pfeil, *Angew. Chem. Internat. Edit.*, 4, 1079 (1965).

Primary Examiner—Charles F. Warren
Assistant Examiner—Carolyn S. Elmore
Attorney, Agent, or Firm—Eugene I. Snyder; Harold N. Wells; Thomas K. McBride

[57] ABSTRACT

A method of homologating monosaccharides via their cyanohydrins utilizes transcyanohydrination across a phase boundary from a water-insoluble donor cyanohydrin dissolved in an organic, water-immiscible solvent to an aqueous solution of a receptor monosaccharide. This heterogeneous transcyanohydrination can be incorporated into a cyclic process where the cyanide donor is enzymatically regenerated via enzyme catalyzed addition of HCN to a suitable aldehyde. The latter process can be made continous or semicontinuous by immobilization of the enzyme.

23 Claims, 2 Drawing Sheets

ONE CARBON HOMOLOGATION OF CARBOHYDRATES BY TRANSCYANOHYDRINATION

CROSS REFERENCE TO RELATED APPLICATIONS

This application is a continuation-in-part of my prior copending application, Ser. No. 810,627, filed Dec. 19, 1985, now abandoned, all of which is hereby incorporated.

BACKGROUND OF THE INVENTION

Present dietetic needs and perceptions have led to the increased use of artificial sweeteners as a replacement for the "natural" sugars, including sucrose and fructose. Such artificial sweeteners are highly imperfect, including being under continual review for their long term physiological affects, yet their demand has grown unabated. Accompanying their growth as a commercial area with substantial economic impact has been a renewed emphasis on discovering and supplying new artificial sweeteners.

The ideal artificial sweetener would be noncaloric, noncariogenic, without detrimental physiological effects, and usable by diabetics. All these requirements would be met if a sweetener were not metabolized by humans and by flora which are found in the mouth and intestinal tract, and if the sweetener were either not absorbed by humans, or absorbed without effect on any internal organ. That is, the ideal sweetener should be excreted in the same form as when ingested. Another desirable feature is that it have bulk properties similar to sucrose so that it can be substituted for table sugar in many formulations. Recently, and perhaps belatedly, attention has turned toward the L-sugars as desirable artificial sweeteners. It has been known since at least 1946 that L-fructose is sweet (M. L. Wolfrom and A. Thompson, *J. Am. Chem. Soc.*, 68, 791,793 (1946)), and since at least 1890 that L-fructose is nonfermentable (E. Fischer, *Ber. Deutsch. Chem. Ges.*, 23, 370,389 (1890)), hence not metabolized by microorganisms generally metabolizing D-sugars. A reasonable, although not necessarily correct, inference is that it also is not metabolized by humans. Assuming that L-fructose is a sweet nonmetabolite it becomes obvious to use it as a noncaloric sweetener in many formulations. More recently Shallenberger and coworkers have demonstrated that many L-sugars have a sweetness comparable to their L-enantiomorphs. *Nature*, 221, 555 (1969). Cf. R. S. Shallenberger, "The Theory of Sweetness," in Sweeteners and Sweetness, pp 42–50. Ed. by G. G. Birch and coworkers; R. S. Shallenberger and T. E. Acree in "The Handbook of Sensory Physiology," Vol. 4, pp 241–245, Edited by L. M. Beider (Springer Verlag, 1971).

Exploitation of the favorable properties of L-sugars is hindered by their relative unavailability. L-Fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited for economical industrial production. U.S. Pat. No. 4,440,855 presents a flow scheme for the preparation of a mixture of L-glucose and L-mannose. The subject matter of U.S. Pat. No. 4,207,413 is L-sucrose, the enantiomer of ordinary table sugar, which can be hydrolyzed to afford L-fructose and L-glucose.

Whatever are the details of processes, actual or proposed, for the preparation of L-sugars, most employ a one carbon chain extension of a lower L-monosaccharide to gain entry to the family of L-sugars. Several methods are known for a one carbon chain extension or homologation of carbohydrates generally, and of monosaccharides in particular, including condensation with nitromethane and addition of the elements of hydrogen cyanide to form a mixture of cyanohydrins. Based on such factors as cost and range of applicability, it appears to us that addition of the elements of hydrogen cyanide is best adapted to the homologation of carbohydrates, and more particularly to the homologation of L-monosaccharides.

Addition of the elements of hydrogen cyanide is typically effected by reacting a cyanide salt or hydrogen cyanide with an aldehyde or ketone, here a monosaccharide, under slightly basic conditions to afford a cyanohydrin or a mixture of cyanohydrins. Such a procedure has several inherent disadvantages. One is the human and environmental danger posed by the necessity of handling the extremely toxic cyanides, which is further multiplied where hydrogen cyanide is the cyanide source or where it is generated, even in small quantities, during subsequent product mixture processing. Because the cyanide used often is in substantial excess, another disadvantage arises from the need to remove cyanide from the cyanohydrin, and the greater the cyanide coexistent with the cyanohydrin the more onerous the task. Related to, yet distinct from, the cyanide problem is the relatively high concentration of other salts in the product mixture incident to this procedure. Not only must these salts be removed from the aqueous solution containing cyanohydrin, but they must be disposed of in an environmentally acceptable fashion.

An alternative to the direct addition of hydrogen cyanide as described above is transcyanohydrination, i.e., the reaction where a cyanohydrin acts as a donor of the elements of HCN to an aldehyde or ketone which acts as the acceptor of these elements. Such a reaction, which has been known for some time, can be depicted as,

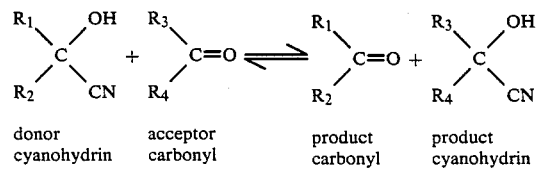

| donor cyanohydrin | acceptor carbonyl | product carbonyl | product cyanohydrin | and in principle can afford mixture free of cyanide and of salts generally. Although cyanide- and salt-free products are rarely attained without the benefit of added purification steps, nonetheless transcyanohydrination is characterized by affording a product mixture containing substantially less cyanide and other salts than present from direct addition of hydrogen cyanide.

Transcyanohydrination as a method of homologation of monosaccharides has not been described, yet there is no impediment to its use. Since carbohydrates generally, and monosaccharides particularly, are freely soluble in water but only difficulty soluble in organic solvents, and because there are good reasons to perform reactions homogeneously (vide infra), a water soluble donor cyanohydrin is indicated. This requirement presents no difficulty, for acetone cyanohydrin is an inexpensive, readily available, and quite water soluble material which can be used as a donor cyanohydrin in the homogeneous transcyanohydrination of carbohydrates generally.

The overwhelming preference for conducting reactions in a liquid state homogeneously (i.e., a single phase) is no whim and rests on sound principles recognized, if not understood, by all chemists at an early stage. In a homogeneous liquid system reagent A is readily transported to reactive site B by diffusion; the reaction rate is rarely transport controlled or even transport influenced. Conversely, in a heterogeneous (i.e., two phase) liquid system the variability of the reaction is legion. Characteristics such as reaction rate, product yield, and product distribution often are reflective of poor transport across the phase boundary and are sensitively affected by the degree of mixing of the two phases. Reproducibility by the same worker is erratic, reproducibility by different workers in the same laboratory is uncertain, and interlaboratory reproducibility frequently is unattainable. It is no accident that heterogeneous liquid state reactions are usually avoided wherever possible.

In accord with the foregoing can be mentioned the work of Kung, U.S. Pat. No. 2,259,167, who prepared relatively low molecular weight cyanohydrins by a homogeneous transcyanohydrination process. In U.S. Pat. No. 4,048,210 Davis recognized that whereas transcyanohydrination could be successfully conducted homogeneously in aqueous solution where water soluble cyanohydrins were formed, an analogous procedure was impossible for his water-immiscible benzaldehydes. To avoid the perceived penalties of a heterogeneous reaction, the patentee constructed a homogeneous transcyanohydrination procedure utilizing an organic solvent.

In view of the well-founded bias against liquid two phase reactions as well as the specific teachings of Davis to avoid heterogeneous transcyanohydrination, my discovery that a heterogeneous variant for homologation of carbohydrates, especially monosaccharides, not only works well but is advantageous and actually is preferred over its homogeneous counterpart is particularly unexpected. The invention herein is a method of homologating monosaccharides employing a heterogeneous, two phase liquid system where the water-insoluble donor cyanohydrin is dissolved in an organic solvent immiscible with water and the acceptor monosaccharide is in aqueous solution. Because hydrogen cyanide or a cyanide salt is not handled, our invention represents a significant advance in worker and environmental safety relative to homologation via direct addition of hydrogen cyanide. Another advantage is that there is demonstrably less cyanide in the product than when direct HCN addition is used. Similarly, the product mixture is far lower in inorganic impurities, mainly salts, in part because pH control can be effected by relatively small amounts of dilute mineral or weak organic acids. This latter consideration is important, for surprisingly it has been found to be far more difficult and costly to remove salts from the product mixture than to separate the formed cyanohydrin from unreacted monosaccharide. Another important advantage unique to our invention is that uncomplicated continuous processes can be readily employed and devised using our two phase, heterogeneous homologation, whereas their counterparts are either more complex or impossible with a homogeneous transcyanohydrination.

Although it should be apparent, it needs to be explicitly recognized and understood that our choice of a heterogeneous transcyanohydrination is a conscious, deliberate one rather than one forced upon us by the exigencies of the situation. Given that the acceptor monosaccharides and their cyanohydrins are water soluble materials insoluble in most organic solvents, it is a simple task to construct a homogeneous aqueous transcyanohydrination process using a water soluble donor cyanohydrin such as acetone cyanohydrin, a readily available compound. What we want to emphasize is that despite the availability of a homogeneous transcyanohydrination process for one carbon homologation of monosaccharides our process is heterogeneous, and that we find such a heterogeneous transcyanohydrination advantageous for the reasons stated in the prior paragraph.

SUMMARY OF THE INVENTION

The purpose of this invention is to provide an alternative method of homologation of monosaccharides. An embodiment comprises a heterogeneous transcyanohydrination where a water insoluble cyanohydrin dissolved in an organic solvent immiscible with water reacts with a monosaccharide dissolved in water with formation of the cyanohydrins of the latter. In a more specific embodiment the donor cyanohydrin is mandelonitrile. In another embodiment the monosaccharide is L-arabinose.

DESCRIPTION OF THE INVENTION

Figure 1:
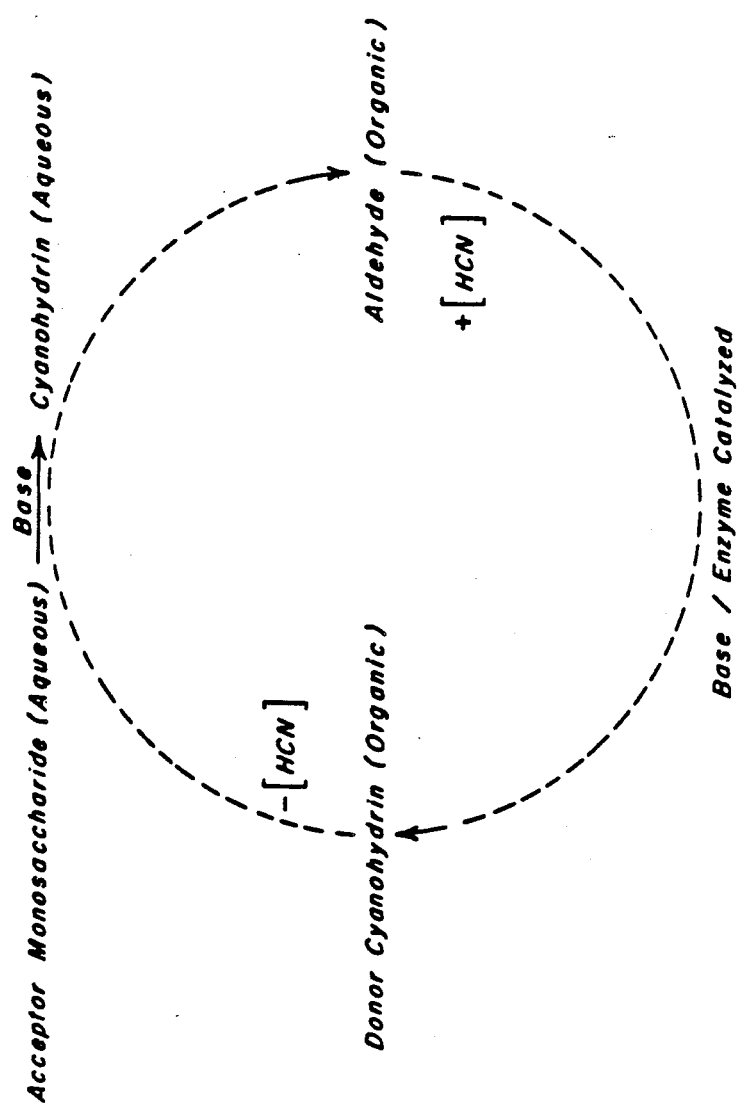
FIG. 1 depicts two phase transcyanohydrination using a donor cyanohydrin dissolved in an organic solvent immiscible with water.

This invention is a method of effecting homologation of carbohydrates generally, and monosaccharides especially, by transcyanohydrination conducted heterogeneously, i.e., in a two phase system. The choice of a heterogeneous reaction, when a homogeneous counterpart is readily available, will be recognized by the skilled worker as a highly unconventional choice whose wisdom is here confirmed by the advantages the process confers. In greater detail, the invention here is the transfer of the elements of hydrogen cyanide from a water insoluble cyanohydrin acting as a donor, dissolved in a water-immiscible organic solvent, to a carbohydrate dissolved in water with formation of the cyanohydrins of the latter. After transfer is completed, the donor cyanohydrin is regenerated either by enzymatic cyanide transfer or by base catalyzed cyanide addition where the former has distinct advantages in a continuous process. The process which is my invention has the advantages of ensuring a low cyanide concentration which is important for safety reasons in cyanohydrin formation with relatively little salt to be removed from the aqueous phase after formation of the monosaccharide cyanohydrins. My invention has the further potential of being conducted as a continuous or semicontinuous process. The overall process is depicted schematically in the Figures.

Any carbohydrate may be conveniently used in the practice of this invention, but monosaccharides are the most usual ones, and among them the tetroses, pentoses, and hexoses generally are the most commonly used monosaccharides. Examples include threose and erythrose, which are tetroses; xylose, lyxose, ribose and arabinose as pentoses; and glucose, mannose, galactose, talose, fructose, allose, altrose, idose, and gulose as illustrative of suitable hexoses. Monosaccharides of either the L or D configuration may be equally well used, although the method which is our invention may prove most useful when the monosaccharide is an L-monosaccharide. A particularly preferred monosaccharide is L-arabinose.

The transcyanohydrination reaction is conducted heterogeneously with the monosaccharide dissolved in water. The monosaccharide concentration is not at all critical, and any convenient concentration which affords a solution of sufficiently low viscosity to ensure adequate contact with the organic phase containing the donor cyanohydrin is acceptable. The product cyanohydrins also are water soluble, which helps to contribute to the success of this invention.

The donor cyanohydrins used in this invention are the reaction products of the addition of the elements of hydrogen cyanide to water insoluble aldehydes, especially aromatic aldehydes, and more particularly benzaldehydes. Examples of aldehydes which can be utilized as the source of donor cyanohydrin include benzaldehyde, substituted benzaldehydes such as alkyl, hydroxy, alkoxy, and halo substituted benzaldehydes, napthaldehyde, anthraldehyde, phenyl acetaldehyde, 3-phenylpropanal, and furfural. Paraffinic aldehydes also may be used so long as they and their cyanohydrins are relatively insoluble in water. Examples of such aldehydes include butanal, pentanal, hexanal, heptanal, octanal, nonanal, decanal, and so forth. Benzaldehyde and hydroxyl-substituted benzaldehydes are particularly favored in the practice of this invention.

It needs to be emphasized that the nature of the aldehyde is not critical to the success of this invention so long as several criteria are met. The aldehyde must readily add the element of hydrogen cyanide in high yield and under mild conditions to form a cyanohydrin. Another criterion is that both it and its cyanohydrin product be soluble in water-immiscible solvents and insoluble in water. By "insoluble" is meant that solubility in water under reaction conditions be less than about 1 weight percent. The cyanohydrin also must readily transfer cyanide to monosaccharides under reaction conditions. Yet another criterion is that both the aldehyde and its cyanohydrin be stable in the context of not undergoing any side reactions in the course of cyanide transfer from the donor cyanohydrin to the monosaccharide. The use of benzaldehydes, both unsubstituted and substituted, is preferred because such aldehydes meet all the foregoing criteria and are relatively cheap and readily available. The use of benzaldehyde itself, with the donor cyanohydrin being mandelonitrile, is particularly preferred.

The formation of the donor cyanohydrin can be effected at a separate site by any means known in the art, such as the base catalyzed addition of the elements of hydrogen cyanide from a cyanide source to the precursor aldehyde. Suitable cyanide sources include cyanide salts, such as those of alkali metals, with sodium and potassium cyanide being favored, as well as other water soluble salts furnishing cyanide ion, and hydrocyanic acid or hydrogen cyanide. The addition of HCN generally is conducted between a pH of about 6 and about 10, but preferably the pH is maintained between about 7.0 and about 9.0, and most preferably between about 7.8 and about 8.2. It has been found that in the absence of this control additional products often are formed which reduce the yield of the donor cyanohydrin, which interfere in subsequent reactions of the process, and which may complicate the isolation of either the donor cyanohydrins or their subsequent reaction products. Control of pH can be conveniently effected by the addition of a weak acid, especially carboxylic acids such as formic acid, acetic acid, propionic acid, butyric acid, valeric acid, and so on, but also by appropriate amounts of a dilute strong mineral acid, such as sulfuric acid.

Preparation of the donor cyanohydrin may be effected at any convenient temperature. Usually the temperature is maintained between about 10° and about 40° C., more desirably between about 15° and about 30° C., and most desirably between about 20° and about 25° C. It will be recognized by the skilled worker that the particular reaction conditions of temperature, pH, etc. may need to be determined for the particular aldehyde from which the donor cyanohydrin is prepared.

Donor cyanohydrin can also be prepared by enzymatically catalyzed cyanide addition to the precursor aldehyde, which is a somewhat preferred mode. For example, in the presence of the enzyme hydroxynitrile lyase aldehydes and hydrogen cyanide afford hydroxynitriles of high optical purity in excellent yields. See W. Becker, H. Freund, and E. Pfeil, *Angew. Chem. Internat. Edit.*, 4, 1079 (1965). Any enzyme which catalyzes cyanide addition may be used in preparation of the donor cyanohydrin, including hydroxymandelonitrile lyase. Enzyme-catalyzed cyanide addition affords the added potential of a continuous process via enzyme immobilization.

The process of transcyanohydrination is carried out simply by vigorously mixing a solution of the donor cyanohydrin in an organic solvent immiscible with water with an aqueous solution of the monosaccharide. Since the reaction is heterogeneous, i.e., the elements of hydrogen cyanide are transferred across a phase boundary, mixing must be vigorous to ensure adequate contact between the immiscible organic and aqueous phases.

The organic solvent is water-immiscible, which is virtually its only restriction and qualification. It is preferred that the solvent be relatively cheap and relatively low boiling, dissolving both the donor cyanohydrin and its precursor aldehyde. Examples include polyhalogenated hydrocarbons such as chloroform, methylene chloride, carbon tetrachloride, tetrachloroethylene, and trichloroethane. Paraffins also may be used, among which are pentane, hexane, heptane, octane, nonane, decane, as well as their mixtures. Suitable aromatic hydrocarbons which may be used as solvents include benzene, toluene, xylene, ethylbenzene, propylbenzene, and other alkyl benzenes, as well as halogenated aromatics such as chlorobenzene, chlorotoluene, and so forth. Ethers also are suitable in the practice of this invention and include such materials as anisole, phenetole, dipropylether, dibutylether, and furan. Illustrative of some esters which may be used are methyl acetate, ethyl acetate, ethyl propionate, and ethyl butyrate. It needs to be emphasized that the organic solvents cited above are merely exemplary and are by no means exhaustive of those which may be successfully used in the successful practice of this invention.

The monosaccharide is at a convenient concentration in aqueous solution. Transcyanohydrination is conducted with the pH of the aqueous solution between about 7 and about 9, especially between about 7.5 and about 8.5 and more particularly at a pH between about 7.8 and about 8.2 At a pH outside this range additional products often are formed which reduce the yield of the cyanohydrins, which interfere in the subsequent reactions of the process, or which may complicate the isolation of either the cyanohydrins or subsequent products thereof. Control of pH can be conveniently effected by the addition of a weak, water soluble acid, especially a carboxylic acid such as formic acid, acetic acid, propionic acid, butyric acid, valeric acid, as well as by dilute solutions of mineral acids such as sulfuric acid. During the reaction the temperature is maintained between about 10° and about 40° C., desirably between about 15° and 30° C., and most desirably between 20° and 25° C.

The heterogeneous reaction mixture containing the donor cyanohydrin in a water immiscible organic solvent as one phase and an aqueous solution of the monosaccharide in a second phase needs to be mixed sufficiently vigorously to provide good contact between the phases so as to effect transfer of the elements of hydrogen cyanide from the donor cyanohydrin to the monosaccharide across the phase boundary with formation of cyanohydrins from the monosaccharide occurring in the aqueous phase and regeneration of the aldehyde precursor to the donor cyanohydrin occurring in the organic phase. When reaction is complete, one can conveniently separate the two phases. The cyanohydrins from the monosaccharide may be recovered from the aqueous phase, and the precursor aldehyde as well as any unreacted donor cyanohydrin may be recovered from the organic phase. The precursor aldehyde either alone or with unreacted donor cyanohydrins then may be recycled so as to regenerate donor cyanohydrin by addition of the elements of hydrogen cyanide to the aldehyde.

Figure 2:
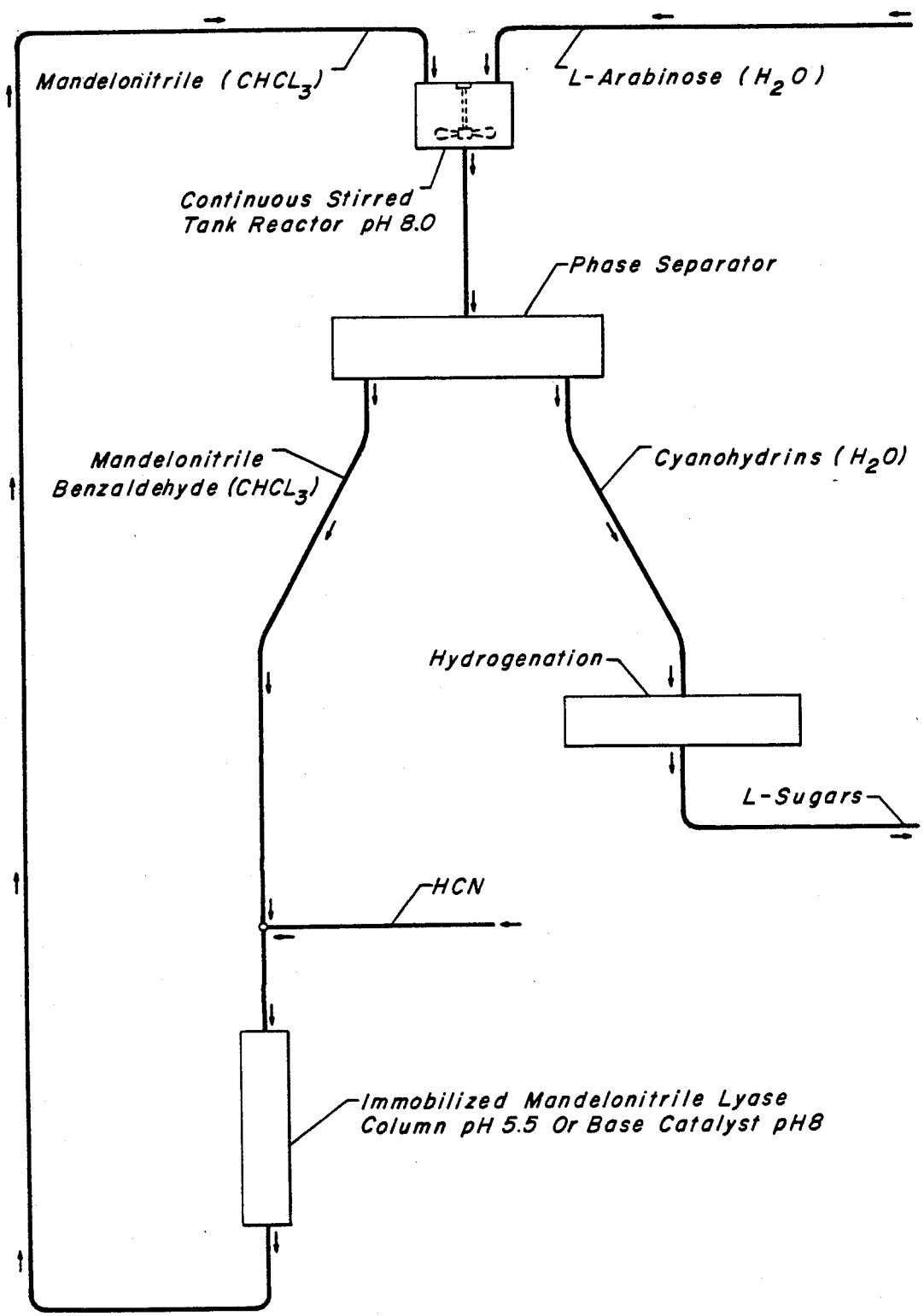
FIG. 2 shows a flow diagram for a continuous transcyanohydrination process using a solution of mandelonitrile in chloroform and an aqueous solution of L-arabinose as representative reactants.

FIG. 2 depicts one of many flow schemes that can be used to catalyze continuous transcyanohydrination. L-arabinose is used only in a representative capacity, and the diagram applies to monosaccharides generally as mentioned above. Similarly, mandelonitrile, chloroform and benzaldehyde only exemplify the cyanohydrin donors, solvents and precursor aldehydes, respectively, which were described more fully above.

In this process an aqueous solution of a monosaccharide is vigorously mixed with a water-insoluble donor cyanohydrin, either dissolved in an organic solvent or neat. This mixing occurs in a reactor zone where the pH is maintained at 7 to 9 at a temperature between about 10° and about 40° C. Mixing may take place in any of several reactor types. These would include a stirred tank reactor, cocurrent tube reactor or countercurrent tube reactor. After leaving the reactor, the phases are separated and the aqueous phase is recovered for further processing. The organic phase, containing unreacted donor cyanohydrin and its water-insoluble aldehyde precursor, is directed toward a regeneration reactor where the direct addition of HCN to the aldehyde regenerates the original donor cyanohydrin. The HCN addition can be catalyzed by either hydroxide or an enzyme. The regenerated donor cyanohydrin is then recycled for further reaction with the monosaccharide in the first reactor zone.

The following examples are only illustrative of my invention which is not to be limited thereto.

EXAMPLE 1

Enzyme Catalyzed Addition of Cyanide to Benzaldehyde

Five ml of a 3.2% aqueous solution of NaCN, adjusted to pH 5.4 with $H_2SO_4$, was mixed with 0.36 g of benzaldehyde to form a suspension and 575 units of the enzyme mandelonitrile lyase in 3.2 $M(NH_4)_2SO_4$ solution was added at room temperature. Within 5 minutes quantitative conversion of benzaldehyde to mandelonitrile was complete.

Transcyanohydrination Reaction

In a 1 liter round bottom flask equipped with a stirrer was placed a solution of 150 ml of chloroform containing 44 g of mandeloitrile. To this was added 75 g of a 33% aqueous solution of L-arabinose. The initial pH of the stirred two phase system was 4.0 and was adjusted to pH 8.0 with concentrated sodium hydroxide. The mixture was stirred for 0.5 hours during which the pH was maintained at 8.0 0.1 with occasional additions of concentrated acetic acid. At the end of this time the mixture was acidified to pH 3.0 with concentrated $H_2SO_4$ and the aqueous layer was separated from the chloroform layer. $^{13}C$ NMR of the aqueous layer showed high conversion (70%) of the L-arabinose to a mixture of L-glucocyanohydrin and L-mannocyanohydrin.

EXAMPLE 2

Effect of Mandelonitrile: Arabinose Ratios and Agitation on Conversion and Selectivity A series of transcyanohydrination reactions were conducted to observe the effects on conversion of mandelonitrile: L-arabinose ratio, reaction time, and degree of agitation. Each was conducted in a 1 L round bottom flask equipped with a constant temperature jacket, stirring motor and pH monitor. In a typical experiment, 25 g of L-arabinose was dissolved in 50 mL of deionized water. This solution was then mixed with 150 mL of chloroform containing varying concentrations of mandelonitrile depending on the desired mandelonitrile to L-arabinose ratio. This mixture was maintained at 20° C.±1.5° C. and pH 8.0 by periodic additions of sodium hydroxide or sulfuric acid as required during the reaction. When desired time had elapsed the reaction was quenched with the addition of sulfuric acid to pH 1.5 with cooling. The aqueous layer was then separated and analyzed by HPLC for L-arabinose and cyanohydrin concentration. The results of these reactions are presented below where "poor" agitation represents mixing with a magnetic stirring bar, and "good" agitation represents mixing by a motor driven impeller.

FIG. 1

| Mandelonitrile: | | | | | | | |
|---|---|---|---|---|---|---|---|
| L-Arabinose | 2:1 | 2:1 | 2:1 | 2:1 | 2:1 | 6:1 | 6:1 |
| Reaction Time (minutes) | 18 | 37 | 195 | 37 | 1200 | 37 | 60 |
| Agitation | poor | poor | poor | good | good | good | good |
| L-Arabinose Conversion | 40.2% | 45.7% | 74.5% | 65.1% | 88.9% | 79.3% | 88.6% |
| Cyanohydrin Selectivity | 100% | 98% | 60% | 93% | 64.9% | 94.8% | 83.6% |

These data show that with proper agitation close to 90% conversion of L-arabinose can be attained within about one hour using a 5-fold excess of mandelonitrile. With such an excess of cyanohydrin selectivities on the order of 85–95% are observed, with selectivity decreasing with increased reaction time.

EXAMPLE 3

Dissociation of Mandelonitrile in a Chloroform-Water Mixture

An experiment was carried out which was a duplicate of the first column in Example 2 except that no L-arabinose was dissolved in the aqueous phase. The aqueous layer was separated from the mixture and found to contain an amount of cyanide equivalent to 3 mole percent of the starting mandelonitrile, whereas when the chloroform layer was analyzed it was shown to contain 15 mole percent benzaldehyde. This demonstrates that most of the cyanide formed via dissociation does not go into the aqueous phase.

EXAMPLE 4

Comparison of Product Compositions

To compare product compositions of direct cyanide vs. transcyanohydrination two reactions were conducted. The transcyanohydrination was exactly as described in Example 2, column 6. The direct cyanide addition was performed as follows. Into a 60 L reactor was charged 18.75 L water and 6415 g of potassium cyanide. The pH of this solution was adjusted to 8.0 with the addition of 4963 g of sulfuric acid with cooling. To this solution was charged 12,363 g of a 60 weight percent aqueous L-arabinose solution. The reaction mixture was stirred for 38 minutes while maintaining the pH at 8.0 with periodic additions of sulfuric acid totaling 18.0 g. The reaction was then quenched upon the addition of 260 g sulfuric acid with cooling to bring the pH to 1.5. The product from each of these reactions was analyzed thoroughly with the following results.

| | Heterogeneous Transcyanohydrination | Direct HCN Addition |
|---|---|---|
| Cyanohydrin | 75.2% (area) | 93.4% (area) |
| Arabinose | 20.7 | 3.1 |
| Gluconic Mannonic Acids | 2.9 | 1.6 |
| Lactone | — | 1.3 |
| —CN | 0.14 wt. % | 4 wt. % |
| S | 1.0 wt. % | 3.2 wt. % |
| Na | 0.3 wt. % | |
| K | | 3.3 wt. % |
| Mandelonitrile | Trace* | — |
| Chloroform | 0.5 wt. %* | — |
| Benzaldehyde | 0.3 wt. %* | — |

*Estimate based on known solubilities

These data show that although the yield of cyanohydrins is greater in the direct addition, the presence of various salts and ions in the aqueous phase is also far greater than in the transcyanohydrination. Since arabinose can be readily and cheaply separated from the cyanohydrin products, the presence of 20% arabinose in the transcyanohydrin product mixture is not a serious detriment. In contrast, the separation of salts from the aqueous solution of cyanohydrins is quite expensive, and the greatly reduced salt level, especially the cyanide level, in the product from transcyanohydrination is highly and importantly advantageous.

EXAMPLE 5

Mandelonitrile as a Hydrogenation Catalyst Poison

A series of hydrogenation reactions were carried out on several cyanohydrin products produced by different methods to establish that, with the proper pretreatment, cyanohydrin synthesized via transcyanohydrination can be successfully hydrogenated to glucose and mannose. Hydrogenations were carried out in a rotating sealed glass lined autoclave. In each case 125 mL of cyanohydrin solution was mixed with 1.5 g of 5% Pd/BaSO$_4$ and pressurd to 60 psi H$_2$ at 35° C. and allowed to react for 22 hrs. At the end of this time the reactor was depressured and the contents were analyzed for conversion of cyanohydrin and glucose/mannose yield. The results of several of these experiments are summarized below.

| Cyanohydrin Source | Percent Conversion | Percent Yield Glucose and Mannose |
|---|---|---|
| From Transcyanohydrination | 0 | 0 |
| Direct Cyanide Addition | 100 | 94 |
| Direct Cyanide Addition Saturated with Mandelonitrile | 0 | 0 |
| From Transcyanohydrination Washed with Chloroform | 100 | 73 |

These results show that cyanohydrin produced by transcyanohydrination can be readily converted to glucose/mannose if it is first "washed" with chloroform. These data suggest that traces of mandelonitrile act as a potent catalyst inhibitor which must be removed.

EXAMPLE 6

Base Catalyzed Addition of Cyanide to Benzaldehyde

Mandelonitrile may be formed by dissolving 10 g of sodium cyanide in 100 l of water and adjusting the pH to 8.0 with the addition of concentrated acetic acid. To this solution may be added 10.6 g of benzaldehyde which will form a suspension. The mixture may then be agitated for about 1 hour and the pH maintained at 8.0 until all of the benzaldehyde is converted to mandelonitrile, which will precipitate upon formation. The mandelonitrile thus formed can be used to carry out the transcyanation as described earlier.

EXAMPLE 7

Continuous Process Scheme

The attached FIG. 2 shows a continuous transcyanation unit with continuous donor regeneration. Mandelonitrile and L-arabinose may be continuously admitted to a first reaction zone, such as a stirred tank reactor with pH maintained at 8.0. The product effluent may be directed to a phase separator. The aqueous layer containing the cyanohydrin may be further reacted, as for example, hydrogenated to produce L-sugars, and the chloroform layer may be directed to the mandelonitrile regeneration segment of the process. The chloroform layer, containing benzaldehyde and unreacted mandelonitrile, may be admitted to a second reaction zone, such as a continuous immobilized mandelonitrile lyase column, together with HCN to effect hydrocyanation of benzaldehyde and regeneration of mandelonitrile. The product effluent, which is a solution of mandelonitrile in chloroform, may then be recycled back to the transcyanation reactor.

What is claimed is:

1. A method of transcyanohydrination of a monosaccharide comprising mixing a solution of a water-insoluble donor cyanohydrin in an organic solvent immiscible with water, said donor cyanohydrin being the adduct of the elements of hydrogen cyanide and a water-insoluble aldehyde, with an aqueous solution at a pH between about 7 and about 9 containing at least one monosaccharide so as to effect transfer of the elements of hydrogen cyanide from said donor cyanohydrin to the monosaccharide with formation of the cyanohydrins of the monosaccharide in the aqueous phase and regeneration of the water-insoluble aldehyde in the organic phase, and recovering the monosaccharide cyanohydrins.

2. The method of claim 1 where the monosaccharide is selected from the group consisting of tetroses, pentoses, and hexoses.

3. The method of claim 2 where the tetrose or pentose is erythrose, threose, arabinose, ribose, lyxose, and xylose.

4. The method of claim 3 where the pentose is L-arabinose.

5. The method of claim 2 where the hexose is selected from the group consisting of glucose, mannose, galactose, talose, fructose, allose, altrose, idose, and gulose.

6. The method of claim 1 where the water-insoluble aldehyde is selected from the group consisting of benzaldehyde and substituted benzaldehydes.

7. The method of claim 6 where the aldehyde is benzaldehyde or a hydroxybenzaldehyde.

8. The method of claim 1 where the organic solvent is selected from the group consisting of polyhalogenated hydrocarbons, paraffinic hydrocarbons, and aromatic hydrocarbons.

9. The method of claim 1 further characterized by regenerating the water-insoluble donor cyanohydrin from the water-insoluble aldehyde.

10. The method of claim 9 where the donor cyanohydrin is regenerated by base catalyzed addition of the elements of hydrogen cyanide to an aldehyde.

11. The method of claim 9 where the donor cyanohydrin is regenerated by enzyme catalyzed addition of the elements of hydrogen cyanide to an aldehyde.

12. The method of claim 11 where the enzyme is hydroxynitrile lyase.

13. The method of claim 1 where the pH is between about 7.5 and about 8.5.

14. The method of claim 14 where the pH is between about 7.8 and about 8.2.

15. The method of claim 1 further characterized in that the reaction is conducted at a temperature between about 10° and about 40° C.

16. A method of continuous transcyanohydrination of a monosaccharide comprising vigorously mixing in a first reaction zone a solution of a water-insoluble donor cyanohydrin in an organic solvent immiscible with water, said donor cyanohydrin being the adduct of the elements of hydrogen cyanide and a water-insoluble aldehyde, with an aqueous solution at a pH between about 7 and about 9 containing at least one monosaccharide so as to effect transfer of the elements of hydrogen cyanide from said donor cyanohydrin to the monosaccharide with formation of the cyanohydrins of the monosaccharide in the aqueous phase and regeneration of the water-insoluble aldehyde in the organic phase, recovering the aqueous phase containing the monosaccharide cyanohydrins, sending the organic phase to a second reaction zone wherein a solution of the water-insoluble donor cyanohydrin is regenerated by reaction of said aldehyde with hydrogen cyanide, and recycling the resulting solution of the donor cyanohydrin to the first reaction zone.

17. The method of claim 16 where the monosaccharide is selected from the group consisting of tetroses, pentoses, and hexoses.

18. The method of claim 17 where the tetrose or pentose is erythrose, threose, arabinose, ribose, lyxose, and xylose.

19. The method of claim 18 where the pentose is L-arabinose.

20. The method of claim 17 where the hexose is selected from the group consisting of glucose, mannose, galactose, talose, fructose, allose, altrose, idose, and gulose.

21. The method of claim 13 where the aldehyde is selected from the group consisting of benzaldehyde and substituted benzaldehydes.

22. The method of claim 21 where the aldehyde is benzaldehyde or a hydroxybenzaldehyde.

23. The method of claim 13 where the organic solvent is selected from the group consisting of polyhalogenated hydrocarbons, paraffinic hydrocarbons, and aromatic hydrocarbons.

* * * * *